(12) United States Patent
Lane et al.

(10) Patent No.: US 11,938,355 B2
(45) Date of Patent: Mar. 26, 2024

(54) ULTRAVIOLET GERMICIDAL IRRADIATION MASK

(71) Applicant: Manaflex, LLC, Waikoloa, HI (US)

(72) Inventors: Robert Clinton Lane, Waikoloa, HI (US); Nathan Chidiac, Los Altos Hills, CA (US)

(73) Assignee: Manaflex, LLC, Waikoloa, HI (US)

( * ) Notice: Subject to any disclaimer, the term of this patent is extended or adjusted under 35 U.S.C. 154(b) by 409 days.

(21) Appl. No.: 17/319,049

(22) Filed: May 12, 2021

(65) Prior Publication Data

US 2021/0353971 A1   Nov. 18, 2021

Related U.S. Application Data

(60) Provisional application No. 63/023,857, filed on May 12, 2020.

(51) Int. Cl.
| | |
|---|---|
| *A62B 7/10* | (2006.01) |
| *A41D 13/11* | (2006.01) |
| *A61L 9/20* | (2006.01) |
| *A62B 9/00* | (2006.01) |
| *A62B 9/02* | (2006.01) |

(Continued)

(52) U.S. Cl.
CPC ............ *A62B 7/10* (2013.01); *A41D 13/1184* (2013.01); *A41D 13/1192* (2013.01); *A61L 9/20* (2013.01); *A62B 9/00* (2013.01); *A62B 18/006* (2013.01); *A62B 18/08* (2013.01); *A62B 23/02* (2013.01); *A61L 2209/12* (2013.01); *A61L 2209/14* (2013.01); *A61L 2209/15* (2013.01); *A62B 9/02* (2013.01); *A62B 18/084* (2013.01); *A62B 18/10* (2013.01)

(58) Field of Classification Search
CPC ....... A61L 9/20; A41D 13/1184; A62B 18/02; A62B 18/025; A62B 18/006; A62B 18/045; A62B 18/08; B01J 19/123
See application file for complete search history.

(56) References Cited

U.S. PATENT DOCUMENTS

2010/0037891 A1* 2/2010 Walker ..................... A62B 7/12
                                                        128/201.23
2021/0339061 A1* 11/2021 Fajardo ................... A62B 18/08
(Continued)

FOREIGN PATENT DOCUMENTS

| GB | 2594100 A | * 10/2021 | ......... A41D 13/1184 |
|---|---|---|---|
| WO | WO-2021187721 A1 | * 9/2021 | |
| WO | WO-2021211723 A1 | * 10/2021 | ............... A23L 3/28 |

OTHER PUBLICATIONS

Machine Translation of DESCRIPTION_WO2021187721A1; Aug. 10, 2023 (Year: 2020).*

(Continued)

*Primary Examiner* — Kendra D Carter
*Assistant Examiner* — Mautin I Ashimiu
(74) *Attorney, Agent, or Firm* — WPAT LAW, P.C.; Anthony King

(57) ABSTRACT

A personal protective equipment system including a face mask and an ultraviolet germicidal irradiation stage to irradiate incoming volume of air before being introduced to the user. There is included a flexible printed circuit enclosed within a housing of the face mask, the flexible printed circuit having an array of UV LED circuits. A fan is provided to drive the volume of air through a passage within the mask.

11 Claims, 8 Drawing Sheets

(51) Int. Cl.
  *A62B 18/00* (2006.01)
  *A62B 18/02* (2006.01)
  *A62B 18/08* (2006.01)
  *A62B 18/10* (2006.01)
  *A62B 23/02* (2006.01)

(56) References Cited

U.S. PATENT DOCUMENTS

2021/0370104 A1* 12/2021 VanDerWoude ..... A62B 18/045
2022/0184335 A1*  6/2022 Kenyon ............ A61M 16/0066

OTHER PUBLICATIONS

What is Foam PVC Sheet; Sheet Plastics; https://www.sheetplastics.co.uk/blog/post/what-is-foam-pvc#:~:text=PVC%20foam%20sheet%20is%20a,%2C%20closed%2Dcell%20foam%20structure.; Aug. 14, 2023 (Year: 2021).*

EVA Foam; FoamInsider; https://www.foaminsider.com/materials/eva-foam/; Aug. 14, 2023 (Year: 2023).*

* cited by examiner

ULTRAVIOLET GERMICIDAL IRRADIATION MASK

CROSS-REFERENCE TO RELATED APPLICATIONS

This application claims priority to U.S. provisional patent application No. 63/023,857, filed on May 12, 2020, which is hereby incorporated by reference in its entirety.

FIELD OF THE DISCLOSURE

The present disclosure relates to personal protective equipment, more specifically, a mask having an ultraviolent germicidal irradiation feature.

BACKGROUND OF THE DISCLOSURE

There is a current need for a better and different personal protective equipment.

Known disposable face masks present health hazards because they don't guarantee safety and are not comfortable to wear. It is often difficult for a user to breathe through these known masks. Currently available masks retain heat and moisture that cannot escape. Furthermore, it is often difficult for a user to speak through them.

All referenced patents, applications and literatures are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply. The disclosed embodiments may seek to satisfy one or more of the above-mentioned needs. Although the present embodiments may obviate one or more of the above-mentioned needs, it should be understood that some aspects of the embodiments might not necessarily obviate them.

BRIEF SUMMARY OF THE DISCLOSURE

In a general implementation, a personal protective equipment system includes a mask coupled to an ultraviolet germicidal irradiation (UVGI) stage.

In another aspect combinable with the general implementation, the mask includes a transparent shield.

In another aspect combinable with the general implementation, there can be a frame disposed around the transparent shield.

In another aspect combinable with the general implementation, there can be a first interior volume defined as a space enclosed between the transparent shield and a portion of a user's face during use.

In another aspect combinable with the general implementation, there can be an exit chamber to allow a passage of a volume of air from the first interior volume before leaving through an exhaust opening.

In another aspect combinable with the general implementation, the UVGI (ultraviolet germicidal irradiation) stage can have an air intake, an entry chamber, and a first UV LED circuit array disposed within the entry chamber.

In another aspect combinable with the general implementation, the first UV LED circuit functions to irradiate a volume of air passing through the entry chamber.

In another aspect combinable with the general implementation, wherein the air intake fluidly connects the outside environment to the entry chamber.

In another aspect combinable with the general implementation, alternatively or optionally, there can be a second UV LED circuit that functions to irradiate a volume of air passing through the exit chamber.

In another aspect combinable with the general implementation, there can be a fan in the UVGI to drive the volume of air to pass through the intended personal protective equipment.

In another aspect combinable with the general implementation, the first UV LED circuit array can be disposed on a flexible printed circuit, and the flexible printed circuit is disposed within the frame.

In another aspect combinable with the general implementation, the second UV LED circuit array can be disposed on a flexible printed circuit, and the flexible printed circuit is disposed within the frame.

In another aspect combinable with the general implementation, both the first UV LED circuit array and the second UV LED circuit array can be disposed on the same flexible printed circuit, and the flexible printed circuit is disposed within the frame.

In another aspect combinable with the general implementation, there can be a fan at or near the entry chamber.

In another aspect combinable with the general implementation, there can be a fan at or near the exit chamber.

In another aspect combinable with the general implementation, the contemplated UVGI stage can be disposed within the frame.

In another aspect combinable with the general implementation, the contemplated UVGI stage can be disposed exterior to the frame.

In another aspect combinable with the general implementation, the contemplated UVGI stage is detachably attached to the outside of the mask.

In another aspect combinable with the general implementation, the contemplated UVGI stage is tethered to the mask via a conduit and can be worn on the user's body.

In another aspect combinable with the general implementation, there can be a particulate filter disposed at the intake.

In another aspect combinable with the general implementation, there can be a particulate filter disposed at the exhaust.

In another aspect combinable with the general implementation, there can be a one-way valve disposed at the intake.

In another aspect combinable with the general implementation, there can be a one-way valve disposed at the exhaust.

In another aspect combinable with the general implementation, the first UV LED circuit array can be disposed on a flexible printed circuit, and the flexible printed circuit is disposed within the frame.

Further, it is contemplated that there can be an entry port connecting the entry chamber to the first interior volume.

In one embodiment, there can be an ambient UV LED circuit array disposed on the flexible printed circuit to provide lighting within the first interior volume.

In another aspect combinable with the general implementation, there can be power source such as a battery coupled to the UVGI stage.

In another aspect combinable with the general implementation, there can be a voice amplification device coupled to the frame, wherein the voice amplification device is at least one of a diaphragm, a laminate, a microphone, a speaker.

Certain features that are described in this specification in the context of separate implementations can also be implemented in combination in a single implementation. Conversely, various features that are described in the context of a single implementation can also be implemented in multiple implementations separately or in any suitable subcombination.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

It should be noted that the drawing figures may be in simplified form and might not be to precise scale. In reference to the disclosure herein, for purposes of convenience and clarity only, directional terms such as top, bottom, left, right, up, down, over, above, below, beneath, rear, front, distal, and proximal are used with respect to the accompanying drawings. Such directional terms should not be construed to limit the scope of the embodiment in any manner.

Figure 2:
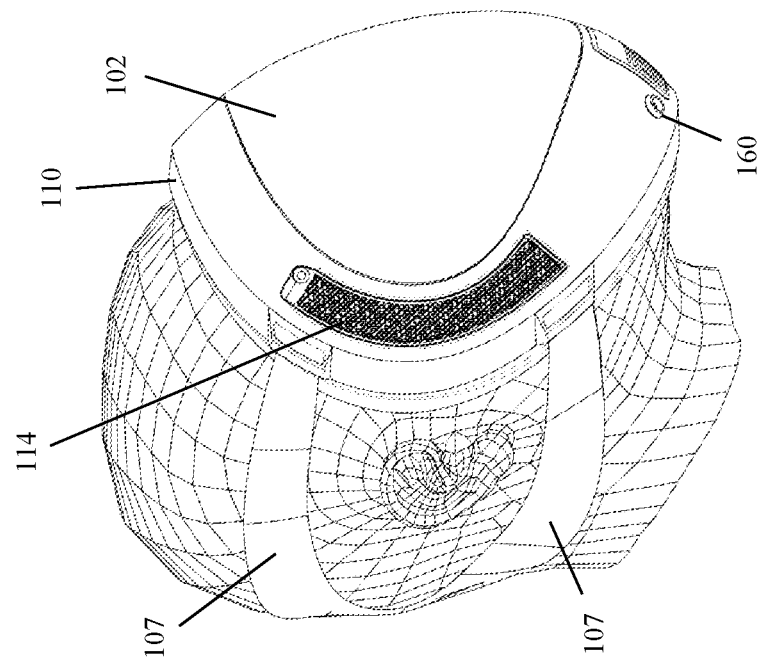
FIG. 2 is a right perspective view of the contemplated face mask of FIG. 1.

The following call-out list of elements in the drawing can be a useful guide when referencing the elements of the drawing figures:

100 Mask
101 UVGI Stage
102 Transparent Shield
103 Magnet
104 First interior volume
105 Conduit
106 Buckle
107 Strap
108 Bulb seal
110 Frame/front plate
112 Back plate
114 Air intake grille
115 Filter
116 Entry Port
117 Entry Chamber
118 Dividing wall
119 Exit Chamber
120 Air flow
121 Air flow
122 Air flow
123 Air flow
124 Air flow
125 Air flow
126 Air flow
127 Air flow
128 Air flow
129 Air flow
130 Air flow
132 Exit Port
133 Exhaust
135 Exhaust Plate
138 Fan
139 Filter
150 Flexible Printed Circuit
152 UV LED
153 UV LED
154 Ambient light LED
160 Accessory connector
170 Battery
172 Microphone
174 Speaker

DETAILED DESCRIPTION OF THE EMBODIMENTS

Figure 1:
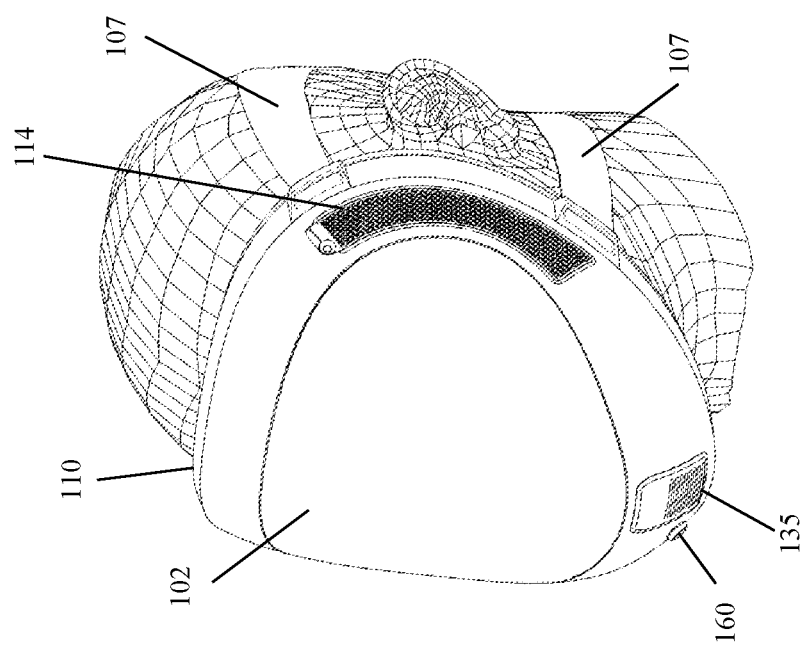
FIG. 1 is a left side perspective view of an embodiment of the contemplated face mask having a UVGI stage disposed within the frame of the face mask.
Figure 3:
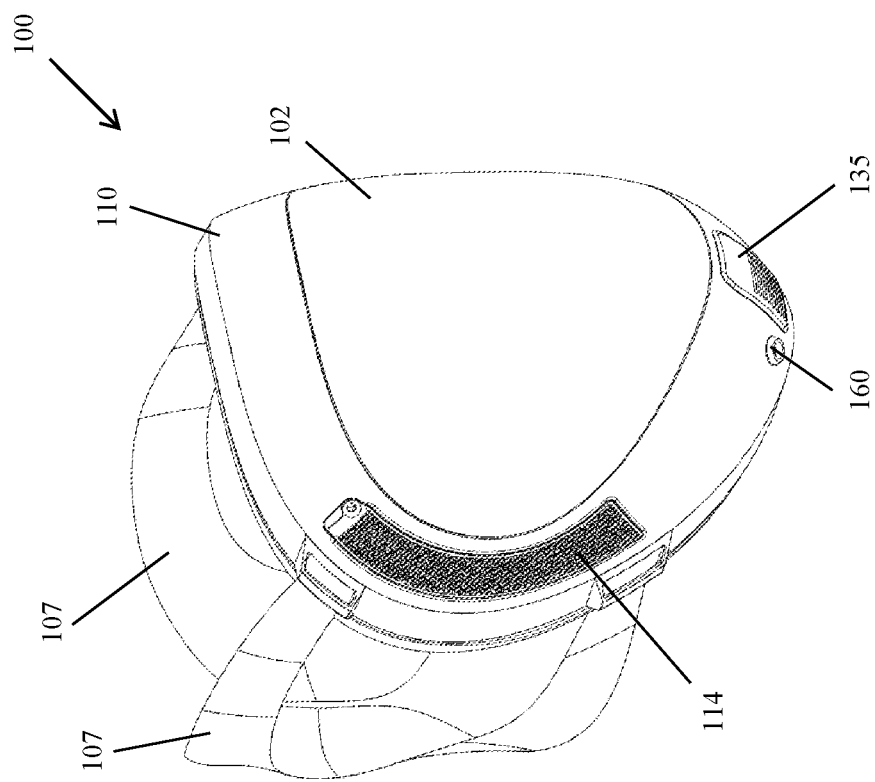
FIG. 3 is another left side perspective view of the contemplated face mask of FIG. 1.

Referring to FIGS. 1-3, a contemplated design for a face mask 100 can have a transparent shield 102 covering a portion of a user's face. In some embodiments, the contemplated transparent shield 102 covers substantially the eyes, the nose, and the mouth of the user. In some embodiments, the mask 100 can be smaller, covering only the nose and mouth of the user.

The transparent shield 102 can be made of various materials known in the art to function as a face shield, whether it is to serve the purpose of having a sturdy permanent utility or for a more cost-effective temporary solution.

The transparent shield 102 can be supported on its perimeter by a frame 110. The frame 110 can be a structural support to keep or somewhat keep the shape and curvature of the transparent shield 102. The frame 110 can be made of a light weight, stiff material (e.g., carbon fiber). The frame 110 can be entirely solid or it can be hollow. In the embodiments shown in FIGS. 1-8, the frame 110 can be made of two complementary pieces consisting of a front plate 110 and a back plate 112. As will be described in more details later, there can be spaces provided between the front plate 110 and the back plate 112 where various components can be embedded.

The contemplated face mask 100 can have at least one air intake. In the embodiments shown on FIGS. 1-3, the two air intakes are each covered with an air intake grille 114. An air intake grille 114 can be a mesh like covering that can be fastened onto the frame 110 via fasteners such as screws. These air intake grilles 114 can be disposed on the lateral sides of the frame 110 and can have a generally elongated shape. Other shapes are also possible. As will be described in more details later, these air intake grilles 114 can optionally have particulate filters 115 attached to them or disposed under them.

There may be straps 107 attached to the frame 110 to help securing the face mask 100 onto a user's head. While FIGS.

1-4 show a pair of arcuate-shaped strap, any known shapes and sizes of straps are also particularly contemplated. Fastening means other than straps can also be implemented. For example, the face mask 100 can be part of a helmet, a full-body suit, or a hat all of which may not require a strap.

The contemplated face mask 100 can have an exhaust 133 covered by an exhaust plate 135. In some embodiments, the exhaust 133 can be located towards the bottom end of the frame 110. In other embodiments, the exhaust 133 can be located elsewhere on the frame 110. The purpose and structural features of the exhaust will be described in more details later.

The embodiments shown in FIGS. 1-3 can also have an optional accessories connector 160, the function of which will be described in more details later.

Figure 4:
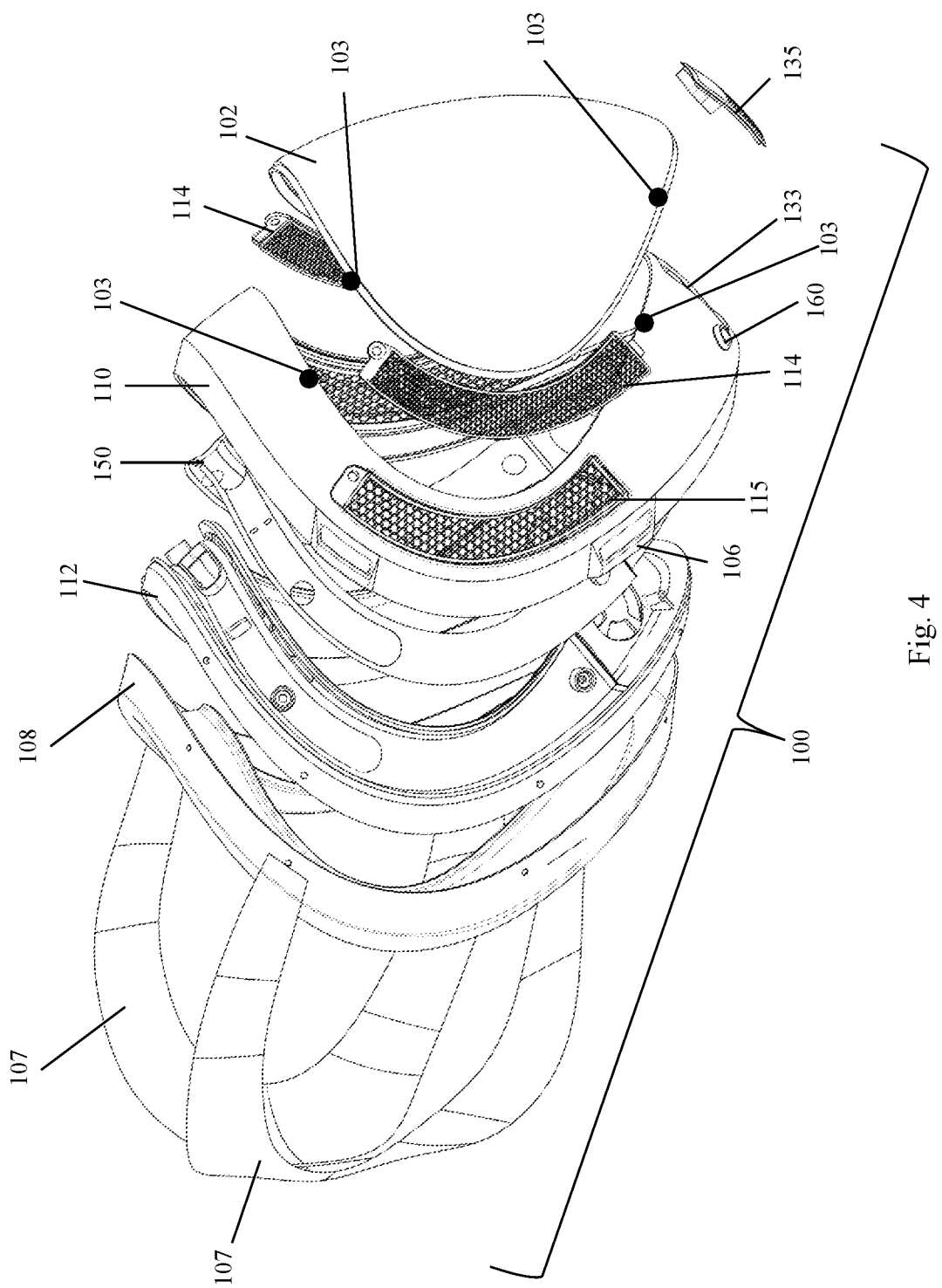
FIG. 4 is an exploded view of one embodiment of the contemplated face mask, according to one aspect of the disclosure.

Referring now to FIG. 4, the transparent shield 102 is shown to be supported by frame 110. Frame 110 provides a structural support surrounding the perimeter of the transparent shield 102. Behind the transparent shield 102 is the first internal volume of space 104 (see FIG. 9) which the user's face is exposed to. The contemplated internal volume of space 104 contains sanitized fresh air supplied from the entry chamber 117 (see FIGS. 5 and 9).

In one particular embodiment, the transparent shield 102 is fixed to the frame 110. In other embodiments, the transparent shield 102 is removably attached or detachably attached to the frame 110. There can be magnets 103 placed in complementary locations on the transparent shield 102 and the frame 110 such that the transparent shield 102 can adhere to the frame 110 due to the magnetic forces. The magnetic force can be sufficiently strong to hold the transparent shield 102 in place during operation, yet sufficiently weak thereby allowing a user to pull the transparent shield 102 off when needed. A user may need to pull the transparent shield 102 off when he/she needs quick access to his/her face for eating/smoking and perhaps during emergency situations. Alternatively, the transparent shield 102 can be pivotably attached to the frame 110 via hinges, thereby allowing user to flip it open.

Referring back to FIG. 4, the outside of the frame 110 can have buckles 106 to which the straps 107 can be attached. Some embodiments may not have buckles 106 and the straps may be fastened to the frame 110 by other means such as fasteners (not shown) and adhesives (not shown). In the embodiment shown in FIG. 4, the elastic straps 107 pull the frame 110 towards the user's face, facilitating a sealed engagement with the user's face.

Complementary to the frame 110 is a back plate 112. The back plate can be fastened to the frame 110 using fasteners or snap-and-lock mechanisms. Other fastening means are also contemplated.

There can be a ring of bulb seal 108, or foam seal disposed on the back plate 112. The bulb seal 108 is pressed against the user's face, making a tight seal such that the volume of air within the first volume 104 does not escape except through the exhaust 133. It should be noted that the straps 107 in FIG. 4 is not directly attached to the bulb seal 108. The straps 107 are attached to the buckles 106 of the frame 110.

In some embodiments, the bulb seal 108 can be any thermally conductive material such as a seal made of filled rubber. The filled rubber can include various known thermally conductive particle and can include graphene, silicon, aluminae. The thermally conductive material can transfer heat from the seal 108 and face interface to the frame 110. The centrifugal fan 138 can help removing heat from the frame 110.

Figure 5:
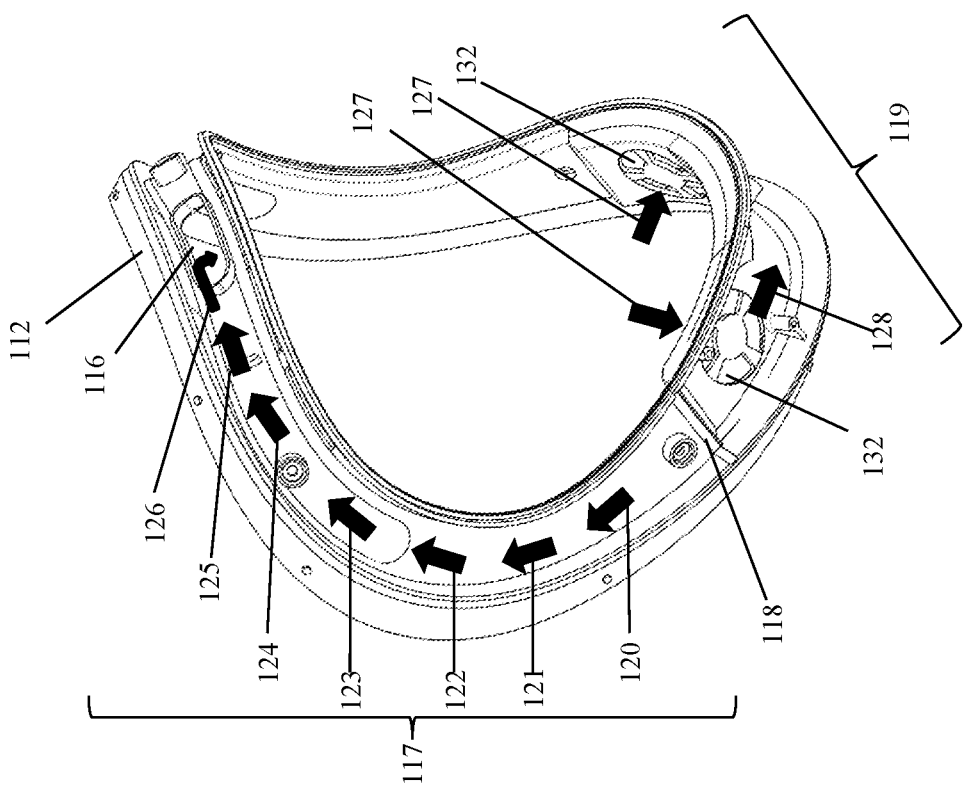
FIG. 5 is a perspective view of one embodiment of a back plate to the frame of the face mask, according to one aspect of the disclosure.
Figure 7:
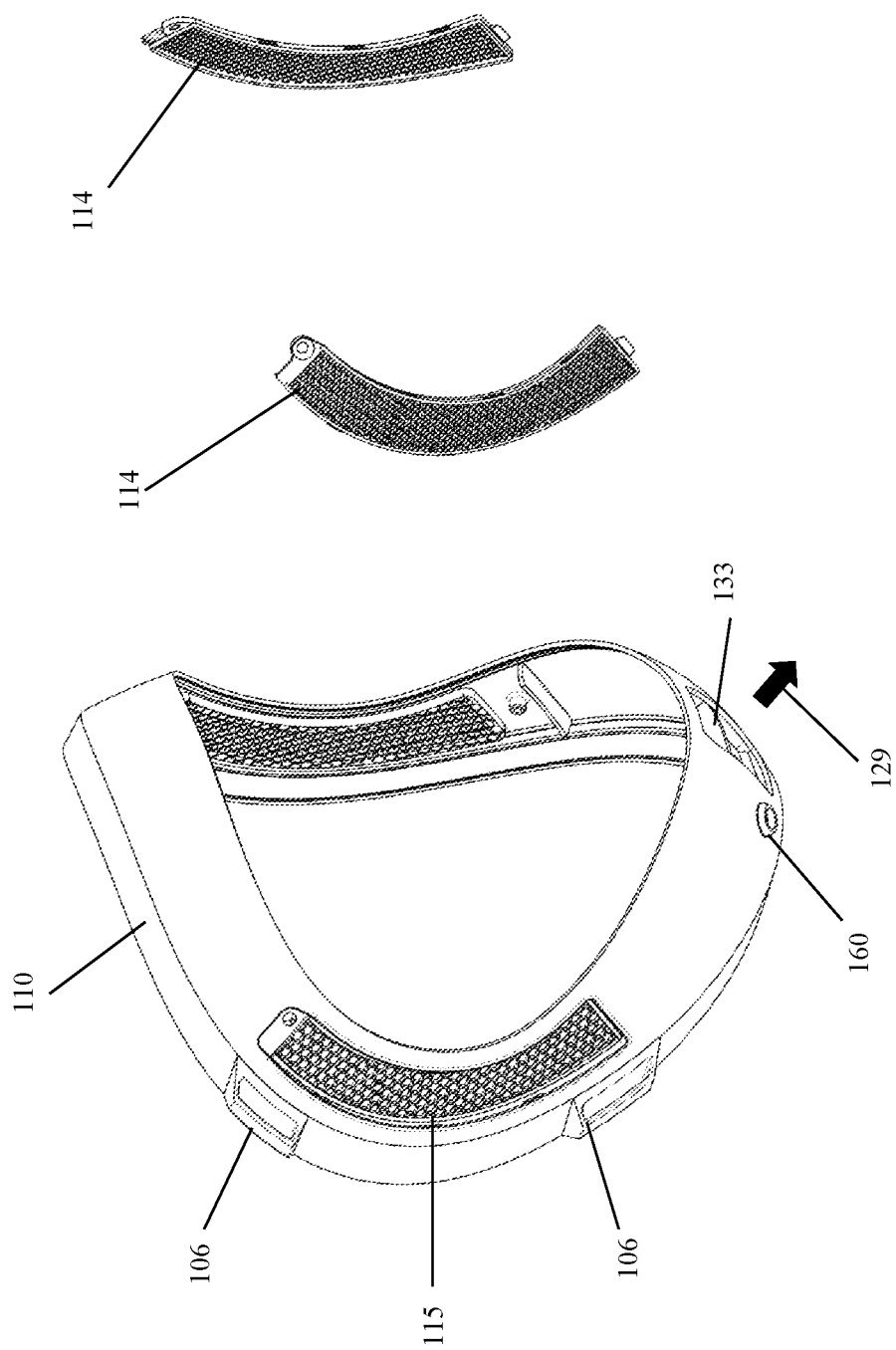
FIG. 7 is a perspective view of one embodiment of the frame and its two intake grilles, according to one aspect of the disclosure.

Relating to the back plate 112, what's important to note in this particular embodiment is that the back plate 112, once fastened onto the frame 110, creates two separate chambers sealed off from each other by a dividing wall 118 (see FIG. 5). The two separate chambers are contemplated to be an entry chamber 117 (see FIG. 5) and an exit chamber 119.

Figure 6:
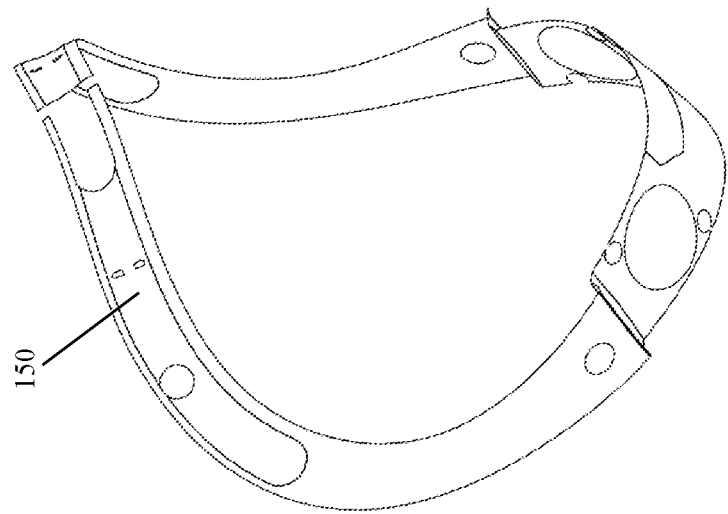
FIG. 6 is a perspective view of one embodiment of a flexible printed circuit that fits within the frame of the face mask, according to one aspect of the disclosure.

Referring now to both FIGS. 5 and 6, the entry chamber 117 can receive a fresh volume of air coming in through the air intake grilles 114. The flow of air generally follows arrows 120, 121, 122, 123, 124, 125, and exits the entry chamber (arrow 126) through entry port 116 to enter into the first internal volume 104.

Contemplated entry port 116 can be an opening of any shape and size. Here, the entry port 116 can be disposed at the top of the back plate 112. In this way, a fresh volume of air can be supplied in a top-to-bottom direction from near the user's forehead. This can be particularly useful to minimize or avoid condensation or fogging of the transparent shield 102.

Prior to this volume of air passing through the entry port 116, however, the volume of air is irradiated with UV light within the entry chamber 117.

The UV irradiation can be achieved by having a first array of UV LED circuits 152 disposed within the entry chamber 117. One aspect of the embodiments provides that this first array of UV LED circuits 152 can be on a flexible printed circuit 150 (see FIGS. 4, 6 and 8). This can be a single stripe of flexible printed circuit 150 that lines the back side of the frame 110, sandwiched between the frame 110 and the back plate 112.

In one contemplated embodiment, this single stripe of flexible printed circuit 150 can be designed to instead line the back plate 112, such that the direction of UV irradiation is from the back plate 112 towards the backside of the frame 110. In this way, there is a less chance UV irradiation entering into the first interior volume 104 through unintended cracks and openings such as the exit ports 132 (see FIG. 5).

Although a single flexible printed circuit 150 is disclosed, the contemplated embodiments are not limited thereto. Multiple flexible printed circuits 150 can be used. In some embodiments, printed circuit boards can be used instead of flexible printed circuit 150.

Figure 8:
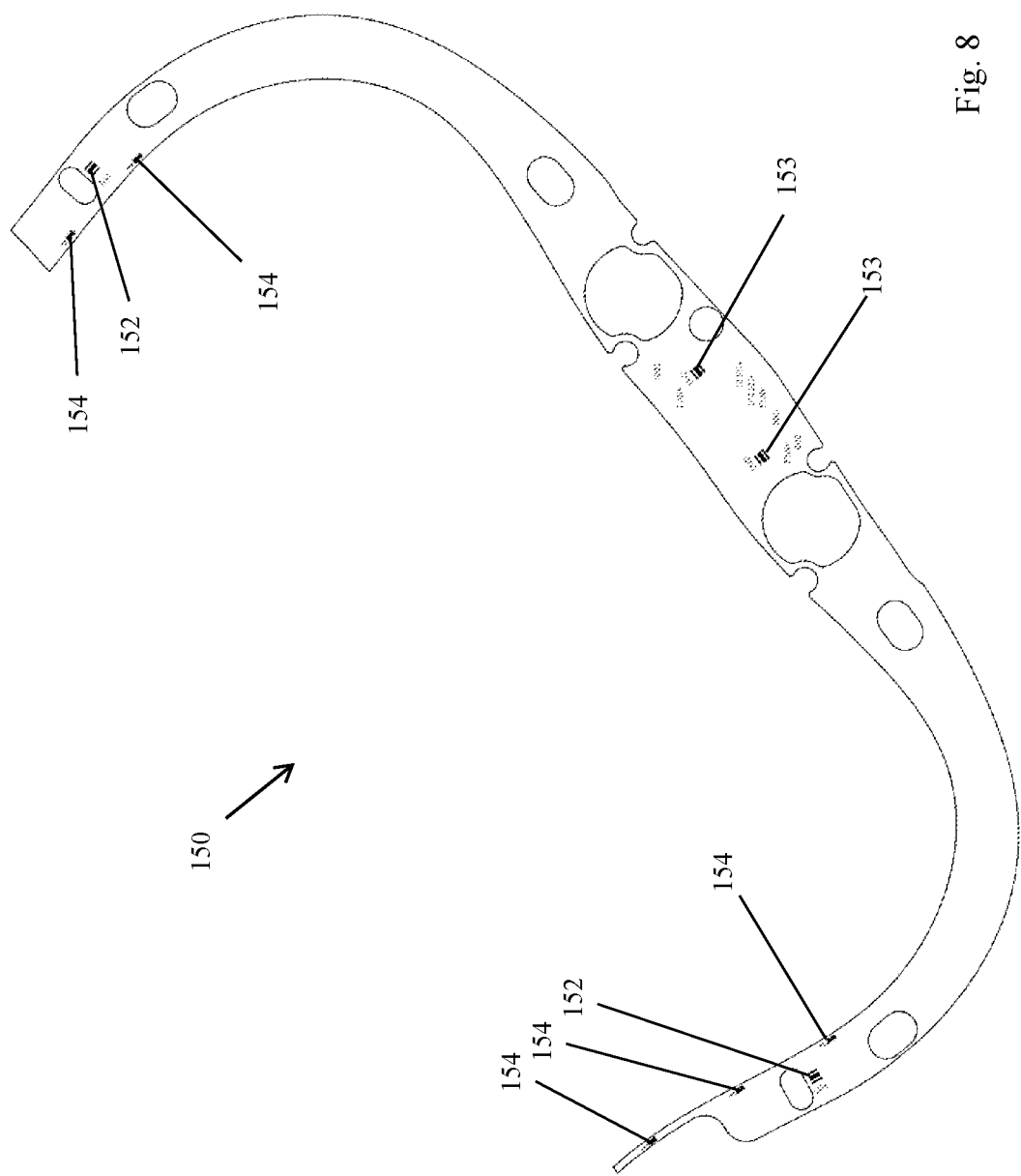
FIG. 8 is a top view of one embodiment of the flexible printed circuit in a flattened state, according to one aspect of the disclosure.

As shown in the exemplar flexible printed circuit 150 in FIG. 8, there are provided a first array of UV LED 152 on the two terminal ends of the single strip of flexible printed circuit 150. When this single stripe of flexible printed circuit 150 is placed between the frame 110 and the back plate 112, the first array of UV LED circuits 152 are disposed within the entry chamber 117. The contemplated first array of UV LED circuits 152 faces the internal space of the entry chamber 117 thereby irradiating the volume of air within this internal space.

Figure 9:
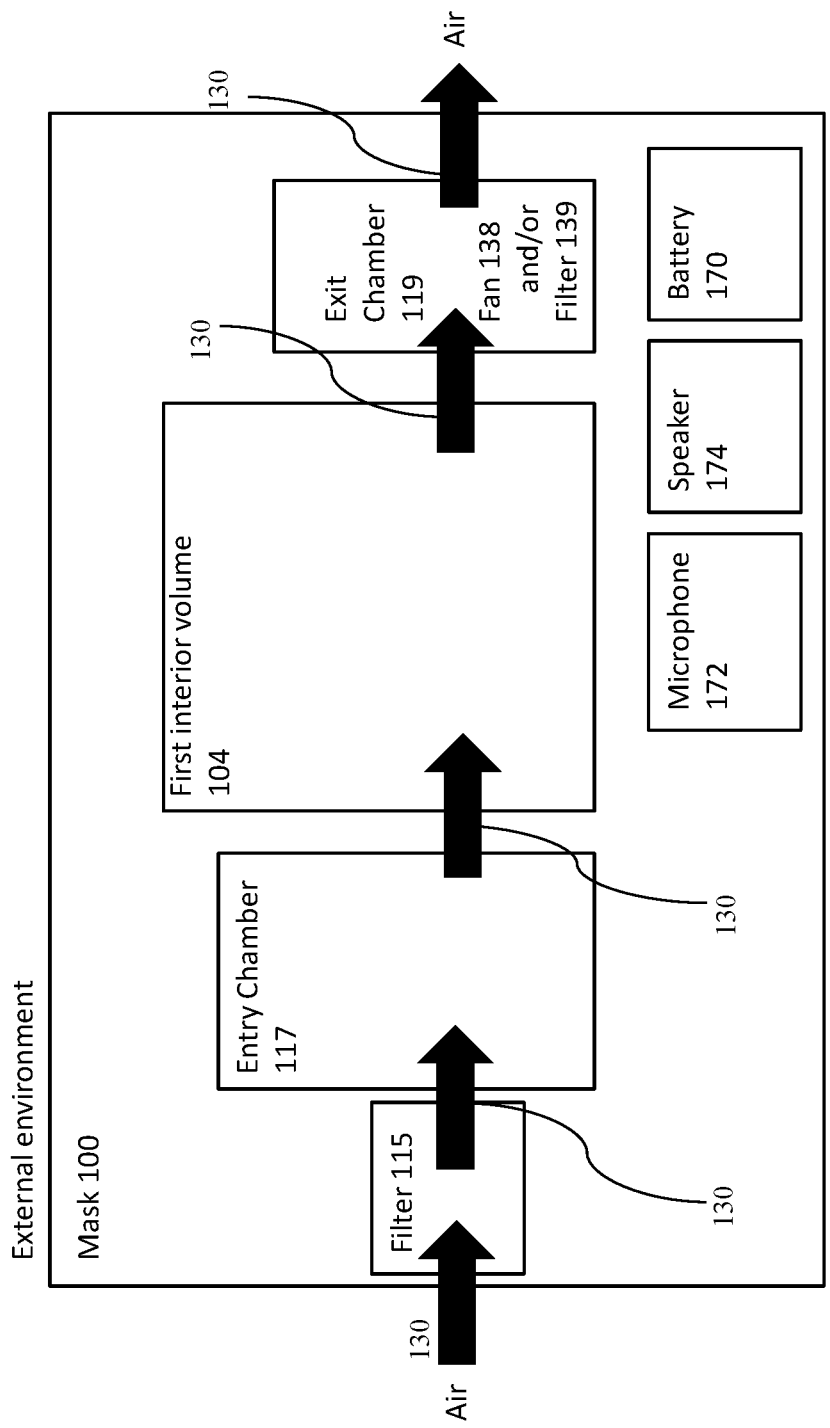
FIG. 9 is a diagram illustrating the flow of air through the contemplated face mask where at least one fan is provided, according to one aspect of the disclosure.

Referring now to FIG. 9, there can be a fan or an air pump coupled to the mask 100 and disposed near the entry chamber 104 (not shown) to actively drive a fresh volume of air from the external environment into the entry chamber 104. Alternatively, there can be a fan 138 disposed near the exhaust end of the air flow to drive the flow of air out of the first interior volume in a forward direction 130. In one embodiment, there can be a centrifugal fan 138 disposed at each of the two circular exit ports 132 (e.g., the left circle and the right circle near the user's mouth).

In some other embodiments, both fans on the front end and at the trail end may be present. In some other embodiments, there can be no fans at all.

While a fan 138 is not required in some embodiments, it would be preferred because of the high differential pressure across the particulate filter 115, if such filter is present.

As the user breathe in the volume of air present in the first interior volume 104, the user also exhales into the first interior volume 104. Air within the first interior volume 104 can exit (arrow 127) through exit ports 132 disposed on the back plate 112 near the mouth of the user.

This volume of air now enters the exit chamber 119 (see arrow 128, FIG. 5), which can be sealingly separate from the entry chamber 117 as describe above.

In some other embodiments, the volume of air may be irradiated here in the exit chamber 119 prior to being released into the external environment. There can be a second array of UV LED circuits 153 disposed within the exit chamber 119 to irradiate a volume of air passing there through. In one embodiment, air is irradiated within exit chamber 119 before being released into the external environment so as to minimize the chance of the user infecting others. In other embodiments, especially where there is no one-way valve provided at the exhaust 133, air within the exit chamber 119 is irradiated to minimize the user breathing in untreated air that unintentionally flow into the first interior volume from the exhaust 133.

This second array of UV LED circuits 153 can be disposed on the same flexible printed circuit 150 where the first array of UV LED circuits are disposed (see FIG. 8). As mentioned earlier, this second array of UV LED circuits can irradiate in a direction from the back plate 112 towards the frame 110 to avoid unwanted UV light entering the first interior volume 104 via exit ports 132.

In some other embodiments, the volume of air may pass from the first interior volume 104 to the external environment through the exhaust 133 without irradiation or filtration. The exhaust 133 can be merely a through opening. In some embodiments, there can be a one-way valve disposed on the exhaust 133 so that air from the external environment cannot enter the first interior volume untreated via the exhaust 133.

In other embodiments, optionally or alternatively to having a second array of UV LED circuits 153, there can be a particulate filter 139 (see FIG. 9) disposed at the exhaust 133 such that the volume of air being released into the external environment is filtered.

Other embodiments of the face mask 100 can include a light source to illuminate the first internal volume 104, or to illuminate the face of the user. This can be achieved by having ambient LED circuits 154 disposed on the flexible printed circuit 150 (see FIG. 8). When the contemplated flexible printed circuit 150 having ambient LED circuits 154 lines the back plate, there can be appropriately placed transparent or semi-transparent windows on the back plate 112 allowing ambient light from the ambient LED circuits to shine through.

In some aspects of the disclosed embodiments, there can be a voice amplification device coupled to the frame 110. In some embodiment, there can be a microphone 172 and a speaker 174 such the user's voice can be transmitted and/or amplified to the external environment. Other known methods of voice amplification can also be used, such as non-electrical means such as laminates or diaphragm to transmit sound.

In still other embodiments, there can be a battery 170 disposed in the mask 100 to provide the necessary current. The battery 170 can be replaceable or can be a rechargeable type.

Figure 10:
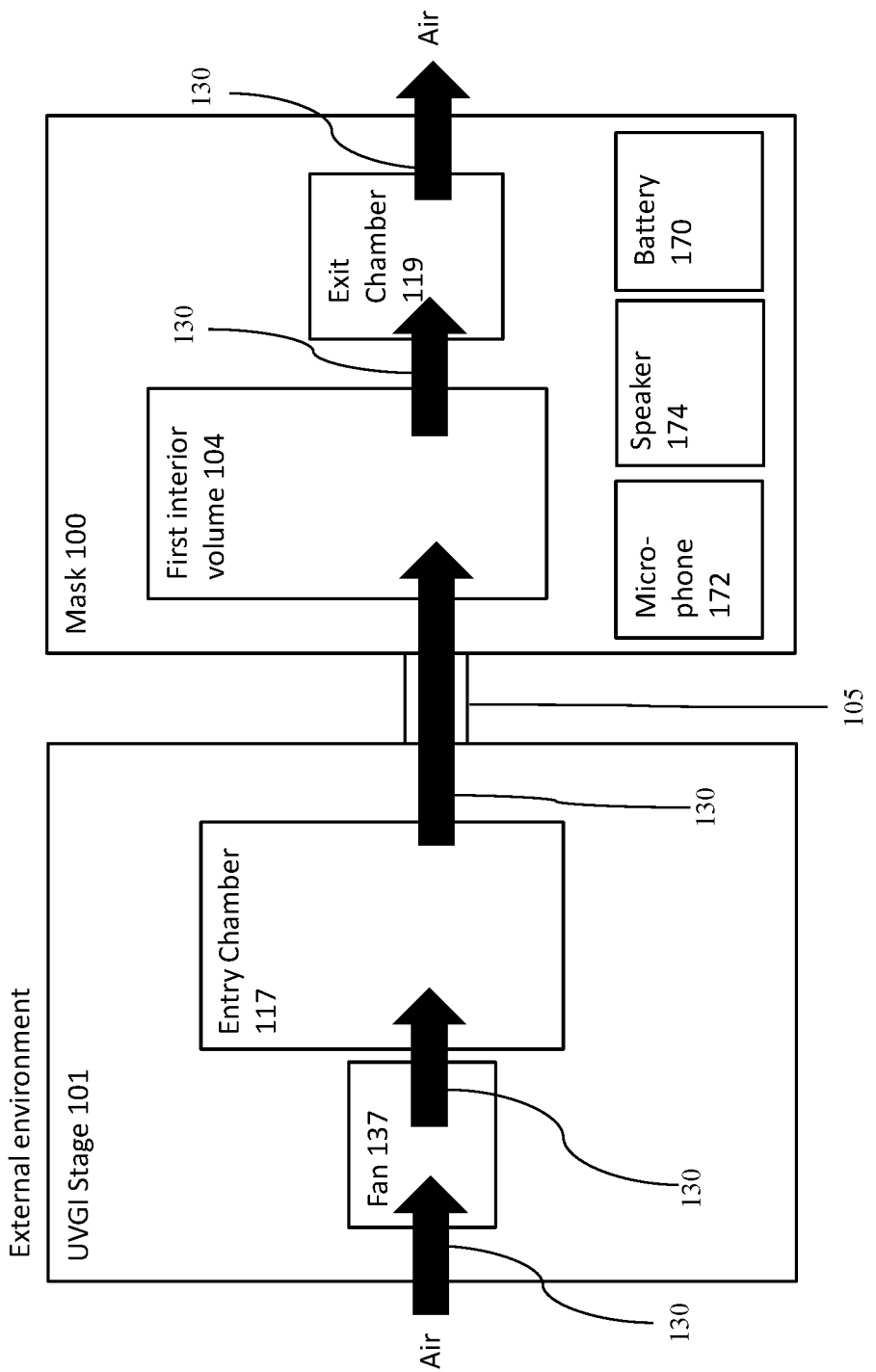
FIG. 10 is a diagram illustrating the flow of air through another contemplated personal protective equipment system where the face mask is coupled to an external UVGI stage via a conduit, according to one aspect of the disclosure.

Referring now to FIG. 10, which illustrates a different embodiment where the irradiation of incoming volume of air is done at a device (e.g., UVGI stage 101) physically separable from the mask 100.

In such embodiments, the mask 100 does not have an entry chamber 117 to irradiate this incoming volume of air. Instead, there can be provided a UVGI (ultraviolet germicidal irradiation) stage 101 to irradiate the incoming volume of air and then pass the air to the mask 100 via a conduit 105.

In one embodiment, this UVGI stage 101 can be worn on the user's body. For example, it can be small enough to clip on a belt. In another embodiment, the UVGI stage 101 can be a standalone unit that is placed on the floor or on a nearly table. This contemplated standalone UVGI stage 101 can be sufficiently large to service more than one masks 100 attached to it, each via a separate conduit 105.

In still yet other embodiments, this UVGI stage 101 can be detachably attached to the outside of the mask 100. For example, it may be small enough and light enough to attach to the top end, the lateral side, or anywhere on the frame 110 of the mask 100.

Similar to the entry chamber 117 described above, the UVGI stage 101 contemplated in FIG. 10 can have a fan 137 to drive outside air to enter into an entry chamber 117. There can be an array of UV LED circuits within the entry chamber 117 to clean the air by exposing the virus and other microbes to enough UV radiation to eradicate virus or other microbes. There can also be an optional filter disposed here in the UVGI stage 101.

Sanitized air is then transferred to the mask 100 via conduit 105.

The UVGI stage 101 of FIG. 10 can be adapted to attach to many other types of known face masks so long as proper connections are made available.

When the air exits from the mask 100 in the embodiment of FIG. 10, the air can also be sanitized by a second array of UV LED circuits as described above. This second array of UV LED circuits may be disposed within the mask 100 as described in the embodiments shown in FIG. 1-9.

The contemplated optional accessories connector 160 can be disposed at the bottom end of the frame 110 as shown in FIGS. 1-4. The accessories connector 160 can provide access to any portion of the mask 100. For example, the accessories connector 160 can be an electrical connector for connecting the microphone 172 to an external speaker (not shown) or a central communication device such that multiple users can communicate via wire. In another example, the accessories connector 160 can connect to external source of power or to an external battery pack. In yet another example, the accessories connector 160 can be designed to connect to a hose where a supply of air can be introduced into the mask 100 through the accessories connector 160.

Furthermore, there may be transmission means in the mask 100 allowing a mask to wirelessly connect to another device, e.g., via Bluetooth.

Many alterations and modifications may be made by those having ordinary skill in the art without departing from the spirit and scope of the disclosed embodiments. Therefore, it must be understood that the illustrated embodiments have been set forth only for the purposes of example and that it should not be taken as limiting the embodiments as defined by the following claims. For example, notwithstanding the fact that the elements of a claim are set forth below in a certain combination, it must be expressly understood that the embodiment includes other combinations of fewer, more or different elements, which are disclosed herein even when not initially claimed in such combinations.

Thus, specific embodiments and applications of ultraviolent germicidal irradiation mask have been disclosed. It should be apparent, however, to those skilled in the art that many more modifications besides those already described are possible without departing from the disclosed concepts herein. The disclosed embodiments, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the embodiments. In addition, where the specification and claims refer to at least one of something selected from the group consisting of A, B, C . . . . And N, the text should be interpreted as requiring at least one element from the group which includes N, not A plus N, or B plus N, etc.

What is claimed is:

1. A personal protective equipment system comprising:
a mask having
a) a transparent shield;
b) a frame disposed around the transparent shield;
c) a first interior volume;
d) an exhaust to allow a passage of a volume of air from the first interior volume to an outside environment;
a UVGI (ultraviolent germicidal irradiation) stage having an air intake, an entry chamber, and a first UV LED circuit array disposed within the entry chamber;
a fan to drive the volume of air from the first interior volume into an exit chamber;
an entry port connecting the entry chamber to the first interior volume; and
wherein the first UV LED circuit array is disposed on a flexible printed circuit and the flexible printed circuit is disposed within the frame;
a second UV LED circuit array disposed on the flexible printed circuit, and the second UV LED circuit array is disposed within the exit chamber;
wherein the air intake fluidly connects the outside environment to the entry chamber;
wherein the UVGI stage is either disposed within the frame or is disposed exterior to the frame;
wherein the exit chamber is disposed within the frame to receive the volume of air from the first interior volume, wherein the exit chamber is connected to the exhaust.

2. The system as recited in claim 1, further comprising an ambient UV LED circuit array disposed on the flexible printed circuit to provide lighting within the first interior volume.

3. The system as recited in claim 1, further comprising a battery coupled to the UVGI stage.

4. The system as recited in claim 1, further comprising at least one filter coupled to the air intake, the exhaust, or both.

5. The system as recited in claim 1, further comprising a voice amplification device coupled to the frame, wherein the voice amplification device is at least one of a diaphragm, a laminate, a microphone, a speaker.

6. The system as recited in claim 1, wherein the UVGI stage is physically separable from the mask and is detachably attached to the exterior of the mask.

7. The system as recited in claim 6, wherein the UVGI stage is coupled to the mask via a conduit.

8. The system as recited in claim 1, wherein the UVGI stage is disposed within the frame of the mask.

9. The system as recited in claim 1, wherein the transparent shield is detachable attached to the frame and can be temporarily removed from the frame during use.

10. The system as recited in claim 1, further comprising an insulating strip disposed on the mask, and the insulating strip includes a thermally conductive material.

11. The system as recited in claim 10, wherein the insulating strip includes filled rubber.

* * * * *